(12) United States Patent
Oren et al.

(10) Patent No.: US 6,866,673 B2
(45) Date of Patent: Mar. 15, 2005

(54) SUTURE MANIPULATING AND/OR CUTTING IMPLEMENT

(76) Inventors: Ran Oren, Kibbutz Gaaton, 25130 Doar Na Oshrat (IL); Dan Moor, Kibbutz Gaaton, 25130 Doar Na Oshrat (IL); Thomas May, 10 George St., Wrentham, MA (US) 02093; Sergio P. Dasilva, 183 Taunton Ave., Norton, MA (US) 02766; Joan M. Sullivan, 61 Old Schoolhouse La., Hanover, MA (US) 02339; Stuart E. Fromm, 3600 Sheridan Lake Rd., #201, Rapid City, SD (US) 57702

( * ) Notice: Subject to any disclaimer, the term of this patent is extended or adjusted under 35 U.S.C. 154(b) by 151 days.

(21) Appl. No.: 10/323,795

(22) Filed: Dec. 20, 2002

(65) Prior Publication Data

US 2004/0122450 A1 Jun. 24, 2004

(51) Int. Cl.[7] ................................................ A61B 17/04
(52) U.S. Cl. ........................ 606/148; 606/144; 289/17
(58) Field of Search ................................ 606/138, 139, 606/144, 148, 103, 113; 289/7, 10, 12, 15, 17

(56) References Cited

U.S. PATENT DOCUMENTS

| | | | |
|---|---|---|---|
| 4,271,838 A | * | 6/1981 | Lasner et al. ............... 606/138 |
| 5,084,058 A | | 1/1992 | Li |
| 5,087,263 A | | 2/1992 | Li |
| 5,133,723 A | | 7/1992 | Li et al. |
| 5,423,837 A | * | 6/1995 | Mericle et al. ............. 606/148 |
| 5,755,730 A | * | 5/1998 | Swain et al. ................ 606/148 |
| 2002/0123758 A1 | | 9/2002 | Bachman et al. |

* cited by examiner

Primary Examiner—Julian W. Woo
(74) Attorney, Agent, or Firm—G. E. Ehrlich, Ltd.

(57) ABSTRACT

An implement for manipulating and cutting a knotted suture includes a body member having a handle at one end, and a knot-engageable section at the opposite end for engaging the knotted suture to be cut; and a cutting member carried by the body member and having an end portion formed with a cutting edge for cutting the knotted suture at a predetermined distance from the knot. The cutting member is movable along its longitudinal axis from a normal position to an actuated position for cutting the knotted suture. The knot-engageable section of the body member is formed with an axial bore for receiving the end portion of the cutting member when the cutting member is moved to its actuated position, and with an angled bore intersecting the axial bore at an angle to the longitudinal axis for receiving the knotted suture. The knot is located at one side of the angled bore and the suture to be cut extends through the angled bore to the opposite side, such as to permit hand-tensioning the knot and then cutting the suture by moving the cutting member to its actuated position.

19 Claims, 2 Drawing Sheets

SUTURE MANIPULATING AND/OR CUTTING IMPLEMENT

FIELD AND BACKGROUND OF THE INVENTION

The present invention relates to a suture manipulating and/or cutting implement, and particularly to a surgical implement for manipulating a knotted suture to properly locate the knot thereof with respect to tissue being sutured, and then for removing excess suture from the knot.

Surgical procedures are increasingly being performed through small portals, or incisions leading directly to the surgical site operated on, thereby minimizing damage to the adjacent tissue. The technique is also known by the name endoscopy. Since the area operated on is not directly visible to the surgeon, the surgeon generally relies on a system of internal illumination and imaging through a small video camera and is guided by an enlarged image generated on a monitor screen.

All necessary operations must therefore be performed through a narrow opening. The size of such an opening limits the size of the instruments used and the free space available to manipulate them. Small-size cutting, grasping, debriding and piercing instruments, capable of operating through small portals, have been developed for this purpose.

Suturing is also possible, and many suture passing and stitching devices are available to the endoscopist. Tying a knot endoscopically remains, however, barely possible. The alternative solution is to use an excess length of suture and to bring the end of the strands to the outside for easy tying. One of several types of sliding knots, similar to the "hangman's knot", is formed at the outside, then moved down the remaining strand through the access portal, and tightened firmly over the tissue stitched. The excess length of suture is then cut off at a small distance above the knot. The length of the suture end remaining after cutting is important: if it is too long, it may cause irritation; if it is too short, the knot may fail to hold.

The steps described above are generally performed by first using a knot manipulator device for pushing the suture, and then a cutting device, such as an endoscopic suture scissors, for cutting off the excess. This is disadvantageous because no "built in" relationship exists between the knot placement and the cutting location. Moreover, introducing a second instrument into the portal leaves little or no room for manipulating it to the desired position.

On the other hand, withdrawing the knot manipulator in order to make room for the cutter makes it difficult and time-consuming to locate the cutter at the right position.

Published U.S. patent application Ser. No. 2002/0123758 A1, published Sep. 5, 2002, by Bachman et al, discloses a surgical knot pushing and cutting device including a pushing interface for pushing a knotted suture to a desired location, and a cutting member for removing excess suture. However, the device described is relatively large in size, and therefore requires relatively large portals or incisions. Moreover, the described device is of relatively complicated construction, and therefore is relatively expensive to produce and complicated to operate.

OBJECTS AND BRIEF SUMMARY OF THE PRESENT INVENTION

An object of the present invention is to provide an implement of the foregoing type having a number of advantages in the above respects, as will be described more particularly below.

According to one aspect of the present invention, there is provided an implement for manipulating a knotted suture to properly locate the knot thereof with respect to tissue being suture, and then for removing excess suture from the knot, the implement comprising: a body member including a handle at one end, and a knot-engageable section at the opposite end for engaging and moving the knotted suture by manipulation of the handle; and a cutting member carried by the body member and movable with respect thereto; the cutting member including a finger-piece at one end proximate to the handle, and a cutting edge at the opposite end proximate to the knot-engageable section of the body member; the finger-piece being movable with respect to the handle from a normal position wherein the cutting edge is disengaged from the suture at the knot-engageable section of the body member, to an actuated position during which the cutting edge engages and cuts the suture at a predetermined distance from the knot, such that the body member may be manipulated to engage the knotted suture and to properly locate the knot with respect to the tissue being sutured, and then the finger-piece of the cutting member may be moved from its normal position to its actuated position to cut the suture at a predetermined distance from the knot and thereby to remove a predetermined excess of the suture; the handle including two loops joined together at one end forming recesses at the juncture which recesses are engageable by two fingers of the user form manipulating the implement.

In the preferred embodiment of the invention described below, the implement further includes a spring biasing the finger-piece of the cutter member to its normal condition.

According to further features in the described preferred embodiment, the body member includes an elongated section between its handle and its knot-engageable section; and the cutting member moves parallel to the longitudinal axis of the elongated section when moved to its actuated position by the finger-piece. The knot-engageable section includes a bore for receiving the knotted suture with the knot located at one side of the bore, and the suture to be cut extending through the bore to the opposite side thereof such as to permit tensioning the knot before cutting the suture.

The bore in the knot-engageable section of the body member for receiving the knotted suture is an angled bore, extending at an angle to the longitudinal axis of the elongated section of the body member. When the cutting member is moved to its actuated position, the cutting edge of the cutting member engages the suture at the juncture of the bore with the longitudinal axis of the elongated section of the body member.

As will be described more particularly below, an implement constructed in accordance with the foregoing features may be used for conveniently manipulating a knotted suture to properly locate the knot with respect to the tissue being sutured, and then, while the implement is still in place, for removing excess suture from the knot. Such an implement can be designed to remove a predetermined length of the suture to assure the suture will hold, but not so long as to cause irritation. An implement constructed in accordance with the foregoing features may also be designed to operate through relatively small portals or incisions.

According to another aspect of the invention, there is provided an instrument for cutting a knotted suture comprising: a body member including a handle at one end and a knot-engageable section at the opposite end for engaging the knotted suture to be cut; and a cutting member carried by the body member and including an end portion formed with a cutting edge for cutting the knotted suture at a predetermined distance from the knot thereof; the cutting member being movable along its longitudinal axis from a normal position to an actuated position for cutting the knotted suture; the knot-engageable section of the body member being formed with an axial bore for receiving the end portion of the cutting member when the cutting member is moved to its actuated position; the knot-engageable section of the body member also being formed with an angled bore therethrough intersecting the axial bore at an angle to the longitudinal axis for receiving the knotted suture, with the knot located at one side of the angled bore and the suture to be cut extending through the angled bore to the opposite side thereof, such as to permit tensioning the knot, and then cutting the suture by moving the cutting member to its actuated position.

Such an implement may therefore be used merely to remove, in a convenient manner, a predetermined excess of suture from the knot.

Further features and advantages of the invention will be apparent from the description below.

BRIEF DESCRIPTION OF THE DRAWING

The invention is described herein, by way of example only, with reference to the accompanying drawings, wherein.

Figure 1:
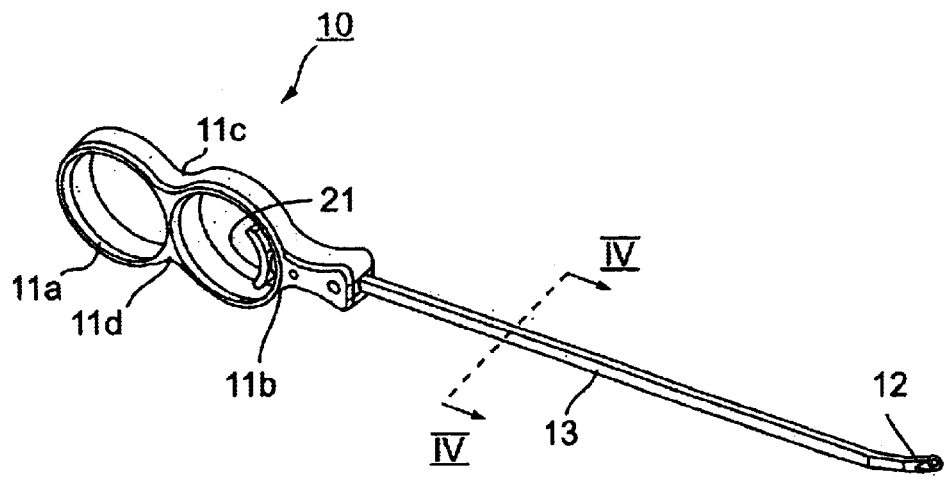
FIG. 1 is a three-dimensional view illustrating one form of implement constructed in accordance with the present invention.

It is to be understood that the foregoing drawings, and the description below, are provided primarily for purposes of facilitating understanding the conceptual aspects of the invention and various possibly embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

The preferred embodiment of the invention illustrated in the drawings is an implement for manipulating a knotted suture to properly locate the knot with respect to tissue being sutured, and then for removing excess suture from the knot.

The illustrated implement includes two main members: a body member, generally designated 10, manipulatable by the user to properly locate the knot of a knotted suture with respect to the tissue being sutured; and a cutting member, generally designated 20, carried by the body member and movable with respect thereto for cutting an excess length of the suture after the knot has been properly located with respect to the tissue being sutured.

The body member 10 includes a handle 11 at one end, defining the proximal end of the implement, and a knot-engageable end section 12 at the opposite end, defining the distal end of the implement. The end section 12 is formed as the angled tip of an elongated intermediate section 13 joined to the handle 11 by a pair of fasteners 14.

Figure 3:
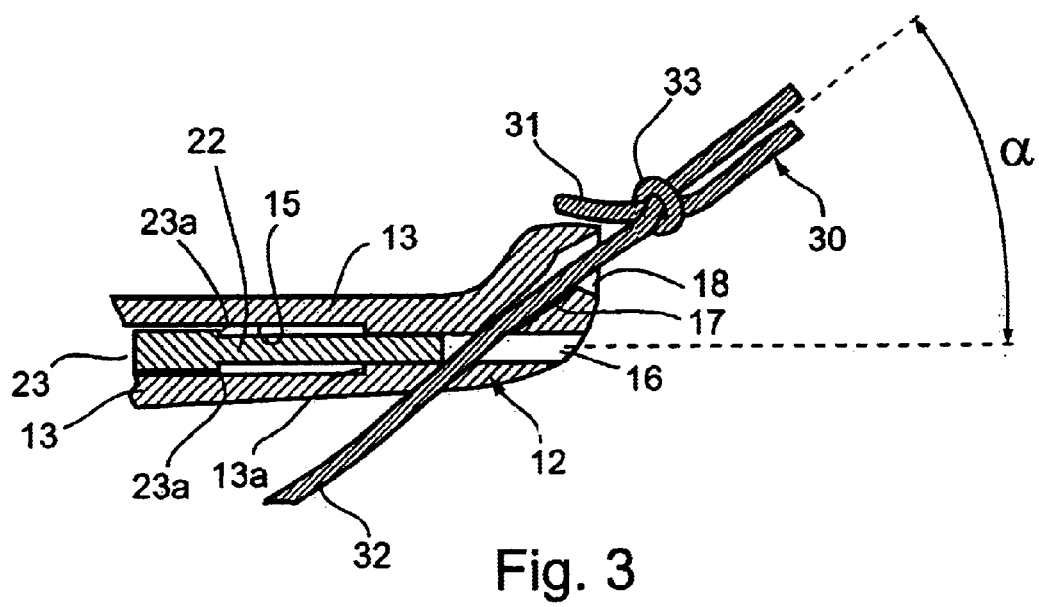
FIG. 3 is an enlarged fragmentary view illustrating the distal end of the implement of FIG. 1 when engaging a knotted suture to be manipulated to a desired location, and then to be trimmed of excess length.
Figure 4:
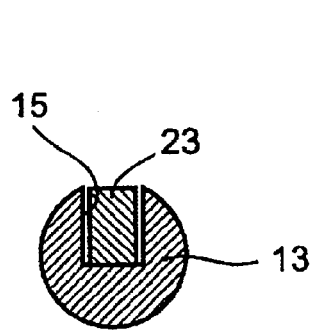
FIG. 4 is an enlarged sectional view long lines iv—iv of FIG. 1.
Figure 5:
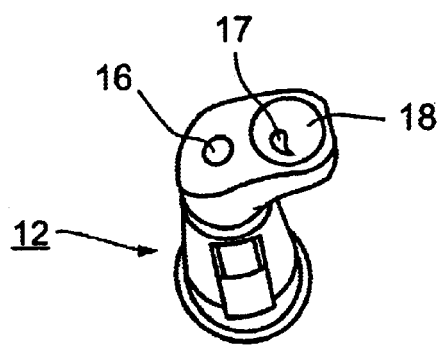
FIG. 5 is an enlarged view of the distal end of the implement of FIG. 1.
Figure 6:
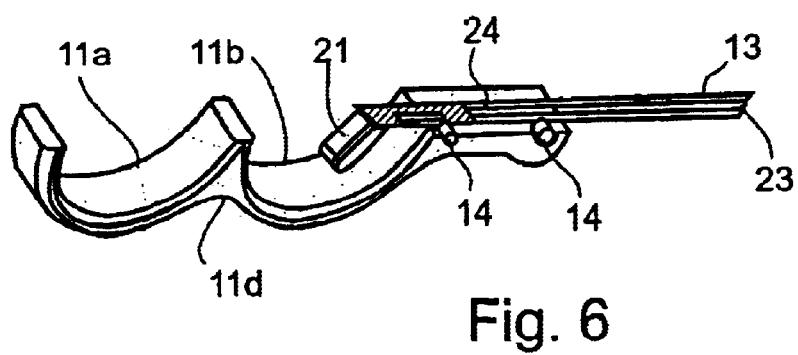
FIG. 6 is a cut-way view of the proximal end of the implement of FIG. 1.

As shown particularly in FIGS. 3 and 4, the elongated intermediate section 13 of body member 10 is formed with an axially-extending slot 15 parallel to the longitudinal axis of body member 10 for receiving the cutting member 20. Slot 15 merges with an axial bore 16, which is coaxial with slot 15 and passes through the end section 12 of the body member. End section 12 of the body member is further formed with an angled bore 17 passing through end section 12 and forms an angle ($\alpha$) with respect to the axial bore 16. Bore 16 is of cylindrical configuration and is coaxial with the longitudinal axis of slot 15 and the elongated section 13 of the body member 10.

FIG. 3 more particularly illustrates the end section 12 of body member 10 for receiving the knotted suture, generally designated 30. As shown in FIG. 3, the knotted suture 30 includes two sutures 31 and 32 tied into a knot 33 which is to be properly located with respect to the tissue being sutured. For this purpose, the outer face of end section 12 pierced by the angled bore 17 is formed with a recess 18 for receiving the knot 33.

As shown in FIG. 3, knot 33 is formed such that one suture 31 has a short surplus length outwardly of the knot 33, whereas the other suture 32 has a long surplus length outwardly of the knot. The long surplus length suture 32 is passed through the angled bore 17 in end section 12 and through axial bore 16, and emerges from the opposite face of the body member 10. As will be described more particularly below, the long surplus end of suture 2 enables the suture to be manually grasped in order to draw its knot 33 into recess 18 of end section 12, and to tension the knotted suture during its manipulation to its proper position with respect to the tissue being sutured. When the knotted suture is so located and still under tension, the cutting member 10 may be manually actuated to cut the suture 32 at the intersection of the angled bore 17 with the axial bore 16, to thereby remove a predetermined excess of suture 32.

Cutter member 20 includes a finger-piece 21 at the proximal end, an end section 22 at the distal end, and an elongated intermediate section 23 coupling finger-piece 21 to the end section. In the assembled condition of the implement shown in FIG. 1, finger-piece 21 is located proximal to the handle 11 of body member 10; the intermediate section 23 is disposed within the elongated slot 15 of the body member; and the end section 22 is aligned with the axial bore 16 formed in end section 12 of the body member.

Cutter member 20 further includes a spring 24 at the proximal end of the implement urging cutting member 20 to its normal position illustrated in FIG. 3, wherein the end section 22 of the cutting member is located within the axial bore 16 on the proximal side of the intersection of that bore with the angled bore 17. End section 22 of cutter member 20 is of cylindrical configuration so as to be movable within axial bore 16, and is formed at its outer face with an annular cutting edge 25, for cutting the suture 32 passing through the angled bore 17.

Figure 2:
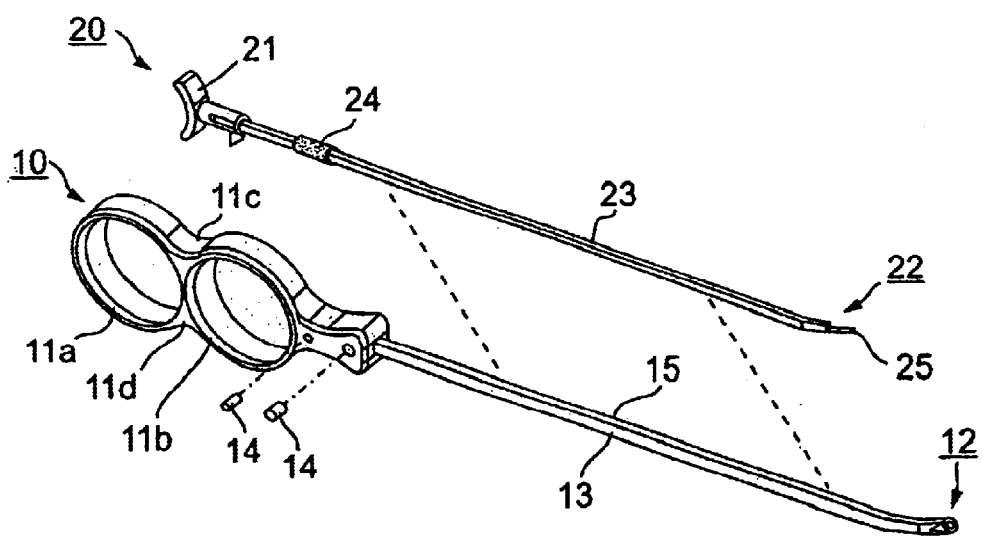
FIG. 2 is a three-dimensional exploded view illustrating the two main members in the implement of FIG. 1.

As shown particularly in FIG. 2, handle 11 of body member 10 is constituted of two 11a, 11b joined together to define recesses 11c, 11d on its opposite faces. The implement may thus be held between two fingers of the user received in the opposed recesses 11c, 11d. When the implement is so held, the user's thumb is located to conveniently engage the finger-piece 21 of the cutting member 20 to actuate the cutting member.

Angle $\alpha$, defined by the intersecting axes of the angled bore 17 and the axial bore 16 in end section 12 of the body member, is preferably 15–75 degrees or, more preferably, 30–60 degrees. A most preferred example would be about 45 degrees.

The manner of using the implement illustrated in the drawings will be apparent from the above description.

Thus, when the implement is in its assembled condition as illustrated in FIG. 1, the knotted suture 30 to be manipulated and cut is passed through the end section 12 of body member 10, such that the knot 33 is received within recess 18, and the long suture 32 passes through the angled bore 17 to the opposite face of the body member, as shown in FIG. 3. Suture 32 may then be grasped by the user and slightly tensioned to firmly seat knot 33 within recess 18 as the implement is manipulated to properly locate the knot with respect to the tissue being sutured. When the knot has thus been properly located, and while tension is still applied to suture 32, finger-piece 21 may be actuated to move the annular cutting edge 25 of the cutting member 20 completely through axial bore 16 to thereby cut the suture 22 at the juncture of the axial bore 16 with the angled bore 17.

Preferably, the juncture of the intermediate section 23 of cutting member 20 with its end section 22, is formed with an annular shoulder, shown at 23a in FIG. 3, engageable with a corresponding shoulder 13a formed in the juncture of elongated section 13 with end section 12 of the body member 10 to limit the actuated position of the cutting member.

It will thus be seen that the implement illustrated in the drawings conveniently enables a knotted suture to be manipulated in order to properly locate the knot with respect to the tissue being sutured; and when so located, it conveniently enables the cutting member 20 to be actuated in order to remove excess suture from the knot. The amount of excess suture removed is fixed by the distance between the outer surface of end section 12 engageable with the knot 33, and the point of intersection of the angled bore 17 with the axial bore 16 first engaged by the cutting edge 25 of the cutting member 20 when that member is moved to its actuated position. Accordingly, this distance can be fixed beforehand to ensure that the suture remaining after cutting is of sufficient length to hold the knot, but not so long as to cause irritation.

While the invention has been described with respect to one preferred embodiment, it will be appreciated that this is set forth merely for purposes of example, and that many variations and other applications may be made. For example, the invention could be embodied in an implement merely for removing excess suture after the knot has been properly located in other manners. Many other variations, modifications and applications of the invention will be apparent.

What is claimed is:

1. An implement for manipulating a knotted suture to properly locate the knot thereof with respect to tissue being sutured, and then for removing excess suture from the knot, said implement comprising:

a body member including a handle at one end, and a knot-engageable section at the opposite end for engaging and moving the knotted suture by manipulation of the handle;

and a cutting member carried by said body member and movable with respect thereto;

said cutting member including a finger-piece at one end proximate to said handle, and a cutting edge at the opposite end proximate to said knot-engageable section of the body member;

said finger-piece being movable with respect to said handle from a normal position wherein said cutting edge is disengaged from the suture at the knot-engageable section of the body member, to an actuated position during which said cutting edge engages and cuts the suture at a predetermined distance from said knot, such that the body member may be manipulated to engage the knotted suture and to properly locate the knot with respect to the tissue being sutured, and then the finger-piece of the cutting member may be moved from its normal position to its actuated position to cut the suture at a predetermined distance from the knot and thereby to remove a predetermined excess of the suture;

said handle including two loops joined together at one end forming recesses at the juncture which recesses are engageable by two fingers of the user for manipulating the implement.

2. The implement according to claim 1, wherein said implement further includes a spring biasing said finger-piece of the cutter member to its normal position.

3. The implement according to claim 1, wherein said body member includes an elongated section between its handle and its knot-engageable section; and wherein said cutting member moves parallel to the longitudinal axis of said elongated section when moved to its actuated position by said finger-piece.

4. The implement according to claim 3, wherein said knot-engageable section includes a bore extending therethrough for receiving said knotted suture with the knot located at one side of said bore, and the suture to be cut extending through said bore to the opposite side thereof such as to permit tensioning the knot before cutting the suture.

5. An implement for manipulating a knotted suture to properly locate the knot thereof with respect to tissue being sutured, and then for removing excess suture from the knot, said implement comprising:

a body member including a handle at one end, and a knot-engageable section at the opposite end for engaging and moving the knotted suture by manipulation of the handle;

and a cutting member carried by said body member and movable with respect thereto;

said cutting member including a finger-piece at one end proximate to said handle, and a cutting edge at the opposite end proximate to said knot-engageable section of the body member;

said finger-piece being movable with respect to said handle from a normal position wherein said cutting edge is disengaged from the suture at the knot-engageable section of the body member, to an actuated position during which said cutting edge engages and cuts the suture at a predetermined distance from said knot, such that the body member may be manipulated to engage the knotted suture and to properly locate the knot with respect to the tissue being sutured, and then the finger-piece of the cutting member may be moved from its normal position to its actuated position to cut the suture at a predetermined distance from the knot and thereby to remove a predetermined excess of the suture;

wherein said implement further includes a spring biasing said finger-piece of the cutter member to its normal position;

wherein said body member includes an elongated section between its handle and its knot-engageable section; and wherein said cutting member moves parallel to the longitudinal axis of said elongated section when moved to its actuated position by said finger-piece;

wherein said knot-engageable section includes a bore extending therethrough for receiving said knotted suture with the knot located at one side of said bore, and the suture to be cut extending through said bore to the opposite side thereof such as to permit tensioning the knot before cutting the suture;

wherein said bore in the knot-engageable section of the body member for receiving said knotted sections is an angled bore and extends at an angle to the longitudinal axis of said elongated section of the body member; and wherein said cutting edge of the cutting member engages said suture, when the cutting member is moved to its actuated position, at the juncture of said bore of the knot-engageable section with the longitudinal axis of said elongated section of the body member.

6. The implement according to claim 5, wherein said elongated section of the body member is formed with an axial passageway is parallel to the longitudinal axis of said elongated section, and wherein said cutting member is movable within said axial passageway to its normal and actuated positions.

7. The implement according to claim 6, wherein said knot-engageable section of the body member is also formed with an axial bore therethrough joined to said axial passageway, said axial bore being configured to receive the end of said cutting member formed with said cutting edge.

8. The implement according to claim 7, wherein said axial passageway in said body member is a slot of rectangular cross-section, and wherein said cutting member is of a corresponding rectangular cross-section except for said end thereof received in said axial bore of the knot-engageable section of the body member.

9. The implement according to claim 8, wherein said axial bore and said end of the cutting member received therein are both of circular cross-section.

10. The implement according to claim 5, wherein said cutting member is formed with a shoulder engageable with a shoulder in said body member after the cutting member has moved its cutting edge past the juncture of said angled bore with said axial bore to cut the suture.

11. The implement according to claim 5, wherein said angle of said angled bore is 15–75 degrees.

12. The implement according to claim 5, wherein said angle of said angled bore is 30–60 degrees.

13. The implement according to claim 5, wherein said knot-engageable section of the body member further includes a recess at said one end of the bore for receiving the knot of said knotted suture.

14. An implement for cutting a knotted suture, comprising:

a body member including a handle at one end and a knot-engageable section at the opposite end for engaging the knotted suture to be cut;

and a cutting member carried by said body member and including an end portion formed with a cutting edge for cutting said knotted suture at a predetermined distance from the knot thereof;

said cutting member being movable along its longitudinal axis from a normal position to an actuated position for cutting said knotted suture;

said knot-engageable section of the body member being formed with an axial bore for receiving said end portion of the cutting member when the cutting member is moved to its actuated position;

said knot-engageable section of the body member also being formed with an angled bore therethrough intersecting said axial bore at an angle to said longitudinal axis for receiving the knotted suture, with the knot located at one side of the angled bore and the suture to be cut extending through said angled bore to the opposite side thereof, such as to permit tensioning the knot, and then cutting the suture by moving the cutting member to its actuated position.

15. The implement according to claim 14, wherein said angled bore forms an angle of 15–75 degrees with respect to said axial bore.

16. The implement according to claim 14, wherein said axial bore and said end of the cutting member received therein are both of circular cross-section.

17. The implement according to claim 14, wherein said cutting member also includes a finger-piece proximate to said handle for moving said cutting member from its normal position to its actuated position, and a spring for normally biasing said cutting member to its normal position.

18. The implement according to claim 14, wherein said body member includes an elongated section between its handle and its knot-engageable section; such elongated section being formed with a slot; said cutting member being movable in said slot from its normal position to its actuated position.

19. The implement according to claim 14, wherein said knot-engageable section of the body member further includes a recess at said one end of the bore for receiving the knot of said knotted suture.

* * * * *